(12) United States Patent
Grodzki (10) Patent No.: US 9,329,253 B2
(45) Date of Patent: May 3, 2016

(54) METHOD TO GENERATE MAGNETIC RESONANCE MEASUREMENT DATA WITH IMAGE CONTRAST SELECTED AND PRODUCED BY PREPARATION PULSES

(71) Applicant: David Grodzki, Erlangen (DE)

(72) Inventor: David Grodzki, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 806 days.

(21) Appl. No.: 13/630,195

(22) Filed: Sep. 28, 2012

(65) Prior Publication Data

US 2013/0082703 A1   Apr. 4, 2013

(30) Foreign Application Priority Data

Sep. 30, 2011 (DE) .......................... 10 2011 083 890

(51) Int. Cl.
| | |
|---|---|
| *G01R 33/56* | (2006.01) |
| *A61B 5/055* | (2006.01) |
| *G01R 33/28* | (2006.01) |
| *G01R 33/48* | (2006.01) |
| *G01R 33/561* | (2006.01) |

(52) U.S. Cl.
CPC ........ *G01R 33/5607* (2013.01); *G01R 33/5602* (2013.01); *A61B 5/055* (2013.01); *G01R 33/288* (2013.01); *G01R 33/482* (2013.01); *G01R 33/4816* (2013.01); *G01R 33/4824* (2013.01); *G01R 33/5615* (2013.01)

(58) Field of Classification Search
CPC ........... G01R 33/5607; G01R 33/5602; G01R 33/288; G01R 33/4816; G01R 33/4824; G01R 33/482; G01R 33/5615; A61B 5/055
See application file for complete search history.

(56) References Cited

U.S. PATENT DOCUMENTS

| | | | |
|---|---|---|---|
| 8,378,678 B2 * | 2/2013 | Schmitt | G01R 33/4818 324/307 |
| 2001/0004211 A1 | 6/2001 | Ookawa | |
| 2004/0061496 A1 * | 4/2004 | Ookawa | 324/307 |
| 2008/0224697 A1 | 9/2008 | Saranathan et al. | |
| 2009/0039885 A1 | 2/2009 | Geppert et al. | |
| 2009/0245607 A1 | 10/2009 | Sugiura | |
| 2010/0205143 A1 * | 8/2010 | Kroeker | G01R 33/4818 707/602 |
| 2013/0119990 A1 * | 5/2013 | Schmitt | G01R 33/4818 324/322 |

* cited by examiner

*Primary Examiner* — Dixomara Vargas
(74) *Attorney, Agent, or Firm* — Schiff Hardin LLP (57) ABSTRACT

In a method and magnetic resonance apparatus to generate magnetic resonance measurement data, k-space corresponding to the examination region is subdivided into a first region and a second region. The first region includes the k-space center, and a ratio of preparation pulses radiated by the radio-frequency antenna of the magnetic resonance apparatus to RF excitation pulses radiated by the radio-frequency antenna is greater in the first region than in a second region of k-space corresponding to the examination region that is not covered by the first region of k-space. Preparation pulses in the entirety of k-space corresponding to the examination region are therefore not radiated uniformly often, but instead a reduced number of preparation pulses is applied in the second region in comparison to the first region. The total measurement time to generate magnetic resonance data, as well as a SAR exposure, are reduced.

11 Claims, 5 Drawing Sheets

METHOD TO GENERATE MAGNETIC RESONANCE MEASUREMENT DATA WITH IMAGE CONTRAST SELECTED AND PRODUCED BY PREPARATION PULSES

BACKGROUND OF THE INVENTION

1. Field of the Invention

The invention concerns a method to generate, by means of a magnetic resonance system, magnetic resonance measurement data of an examination region to be examined that is located in a measurement volume of a magnetic resonance system by radiation of preparation pulses into the examination subject and readout of k-space corresponding to the examination region as well as a magnetic resonance system electronically readable data medium with programming instructions to implement such a method being stored therein.

2. Description of the Prior Art

Magnetic resonance (MR) is a known modality with which images of the inside of an examination subject can be generated. Expressed simply for this purpose, the examination subject is positioned within a strong, static, homogeneous basic magnetic field (also called a $B_0$ field) with field strengths of 0.2 Tesla to 7 Tesla and more, such that the nuclear spins of the examination subject orient along the basic magnetic field. To trigger nuclear magnetic resonances, radio-frequency excitation pulses (RF pulses) are radiated into the examination subject, the triggered magnetic resonance signals are measured (detected), and MR images are reconstructed or spectroscopy data are determined based on these magnetic resonance signals. For spatial coding of the measurement data, rapidly switched magnetic gradient fields are superimposed on the basic magnetic field. The acquired measurement data are digitized and stored as complex numerical values in a k-space matrix. An associated MR image can be reconstructed from the k-space matrix populated with such values, for example by a multidimensional Fourier transformation.

It is possible to depict soft tissue parts with high contrast by means of MR techniques. Different substances can be presented and differentiated well with suitable sequences due to their different physical properties, such as the relaxation time of the longitudinal magnetization T1, the decay time of the transverse magnetization T2, or the time constant of the free induction decay T2* (also called effective decay time of the transverse magnetization), or also precession frequencies.

The achieved image contrast can be additionally, specifically varied by the use of pulses known as preparation pulses (also known as pre-pulses). For example, such preparation pulses are preparation pulses for fat and/or water suppression or T1 or T2 preparation pulses. During the acquisition of the measurement data in the sequences, such preparation pulses are radiated into the examination subject before or in combination with the RF pulses that are used. However, a certain time duration must thereby be allotted for the preparation pulse (and possibly also for a subsequent dephasing of unwanted signals, for example—known as "spoiling") or to relax the nuclear spins in the pulse sequence. Depending on the type of preparation pulse, the measurement time can hereby be markedly extended. In spite of this, in order to keep the measurement time short, preparation pulses are normally radiated only at every m-th excitation and acquisition of measurement data, with m typically being a number between approximately five and approximately 20. However, if m is chosen too large, it is no longer necessarily ensured that the desired contrast is achieved.

SUMMARY OF THE INVENTION

An object of the present invention is to provide a method to generate magnetic resonance measurement data, a magnetic resonance system, and an electronically readable non-transitory data storage medium that shorten the measurement time to acquire MR measurement data with image contrast selected and achieved specifically by the use of preparation pulses, in comparison to the aforementioned methods.

A method according to the invention to generate magnetic resonance measurement data of an examination region of an examination subject that is to be examined (which examination region is located in a measurement volume of a magnetic resonance system) by means of the magnetic resonance system comprises a radiation of preparation pulses into the examination subject and a readout of k-space corresponding to the examination region, includes the steps:

excite echo signals by means of RF excitation pulses successively radiated by a radio-frequency antenna of the magnetic resonance system with different gradients for spatial coding until k-space corresponding to the examination region is read out, wherein a ratio of preparation pulses radiated by the radio-frequency antenna of the magnetic resonance system to RF excitation pulses radiated by the radio-frequency antenna of the magnetic resonance system is greater in a first region of k-space corresponding to the examination region (which first region comprises at least the k-space center) than in a second region of k-space corresponding to the examination region, which second region is not covered by the first region of k-space, acquire echo signals with the radio-frequency antenna after each radiated RF excitation pulse, store the acquired echo signals as magnetic resonance measurement data.

According to the invention, k-space corresponding to the examination region is thus subdivided into two regions (a first region and a second region), wherein one of the regions—the first region—includes the k-space center, and a ratio of preparation pulses radiated by the radio-frequency antenna of the magnetic resonance system to RF excitation pulses radiated by the radio-frequency antenna of the magnetic resonance system is greater in the first region than in a second region of k-space corresponding to the examination region that is not covered by the first region of k-space. Preparation pulses are therefore not radiated uniformly often in the entirety of k-space corresponding to the examination region; rather, in the second region a reduced number of preparation pulses is applied in comparison to the first region.

Due to the reduced number of applied preparation pulses in comparison to the applied RF excitation pulses in the second regions which do not include the k-space center, the total measurement time to scan k-space corresponding to the examination region can be significantly reduced. Moreover, the SAR (Specific Absorption Rate) exposure to the examination subject is likewise reduced since fewer preparation pulses—and therefore less energy—are radiated into the examination subject. Furthermore, noise development caused inside the magnetic resonance system by the gradients to be switched (and eddy currents that are incurred with these) can be reduced since the gradients must be changed less often due to the lower number of preparation pulses in the second regions. In spite of this, the sought image contrast remains largely unaffected since measurement data from the contrast-determining first region which comprises the k-space center are acquired with a sufficient number of preparation pulses. The resolution of the acquired measurement data is also not reduced in total relative to known methods since the number of measurement points in k-space does not need to be reduced.

In various exemplary embodiments, a preparation pulse can be a T1 preparation pulse, or a T2 preparation pulse, or a preparation pulse to suppress unwanted signals (for example fat or water). If the preparation pulse is a T2 preparation pulse, an additional advantage results. Typically, given the use of T2 preparation pulses blurring occurs in the image data reconstructed from the measurement data, which is due to expansion of what is known as the "point spread function" (PSF) that is caused by the T2 preparation pulses. Given the method according to the invention in connection with T2 preparation pulses, such blurrings can be reduced since, in the second region of k-space, fewer T2 preparation pulses (or even no T2 preparation pulses) are radiated in the outer k-space region, which is significant for the sharpness and resolution of the reconstructed MR image, and thus an expansion of the PSF is reduced or avoided entirely.

A magnetic resonance system according to the invention has a basic field magnet, a gradient field system, a radio-frequency antenna; and a control device to control the gradient field system and the radio-frequency antenna, to receive measurement signals acquired by the radio-frequency antenna, to evaluate the measurement signals, and to create magnetic resonance images, and is designed to implement the method described herein.

The above object also is achieved in accordance with the present invention by a non-transitory, computer-readable data storage medium encoded with programming instructions that, when the storage medium is loaded into a computerized control and evaluation system of a magnetic resonance apparatus, cause the magnetic resonance to implement one or more of the above-described embodiments of the method according to the invention.

The advantages and embodiments described with regard to the method analogously apply to the magnetic resonance system, the electronically readable data medium.

DESCRIPTION OF THE PREFERRED EMBODIMENTS

Figure 1A:
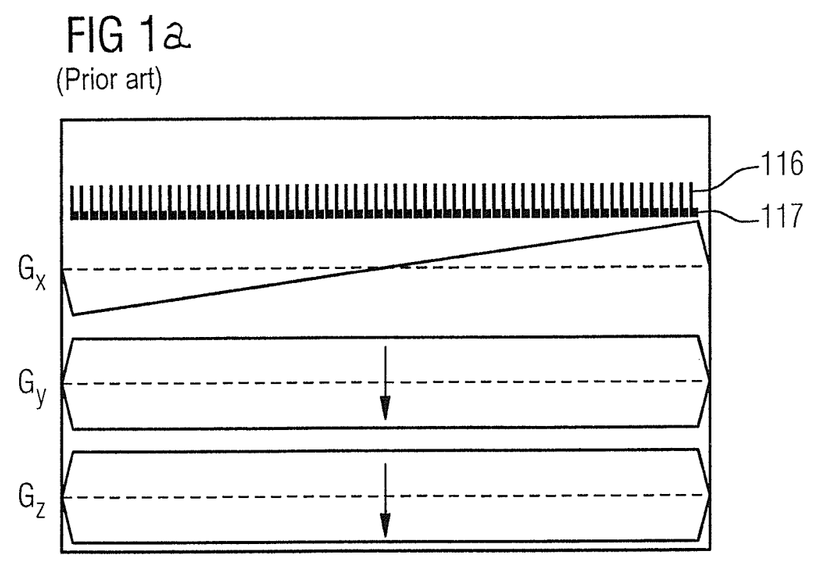
FIGS. 1a and 1b illustrate the RASP method known according to the prior art.

A sequence to acquire a line in k-space is shown in FIG. 1a, according to the known RASP method. It is apparent that the two phase coding gradients $G_y$ and $G_z$ are activated with a constant strength while the strength of the third phase coding gradient $G_x$ increases continuously. For simplicity, no peripheral pulses 115 are drawn in this view.

Figure 1B:
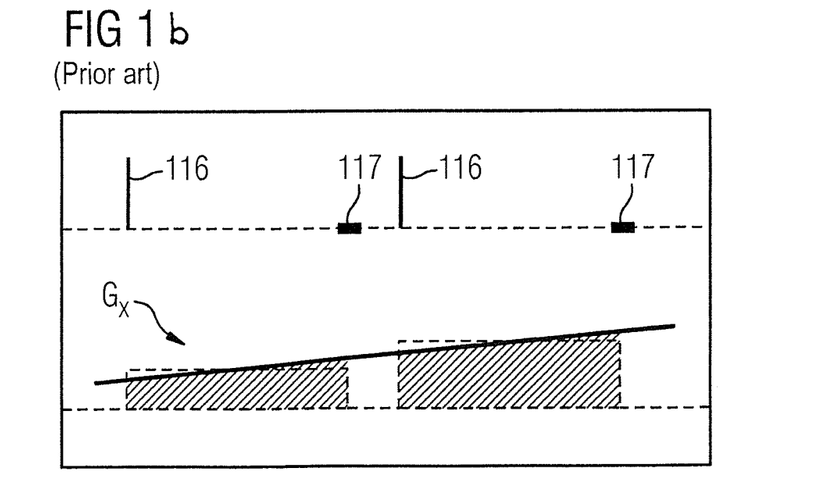

The acquisition of two raw data points in RASP is presented in detail in FIG. 1b. It is apparent that the echo time—i.e. the time interval from the RF excitation pulse 116 up to the beginning of the readout time period 117—is constant. Moreover, the phase coding gradient $G_x$ runs in stages from the bottom upward. The phase coding gradient $G_x$ to read out a raw data point is thereby kept constant, which means that the phase coding gradient $G_x$ is kept constant for the time period TE (echo time). A preparation pulse 115 can be radiated every N RF excitation pulses 116, for example before the respective RF excitation pulse or also in combination with the respective RF excitation pulse, wherein N is a number provided by a user of the magnetic resonance system.

Figure 2:
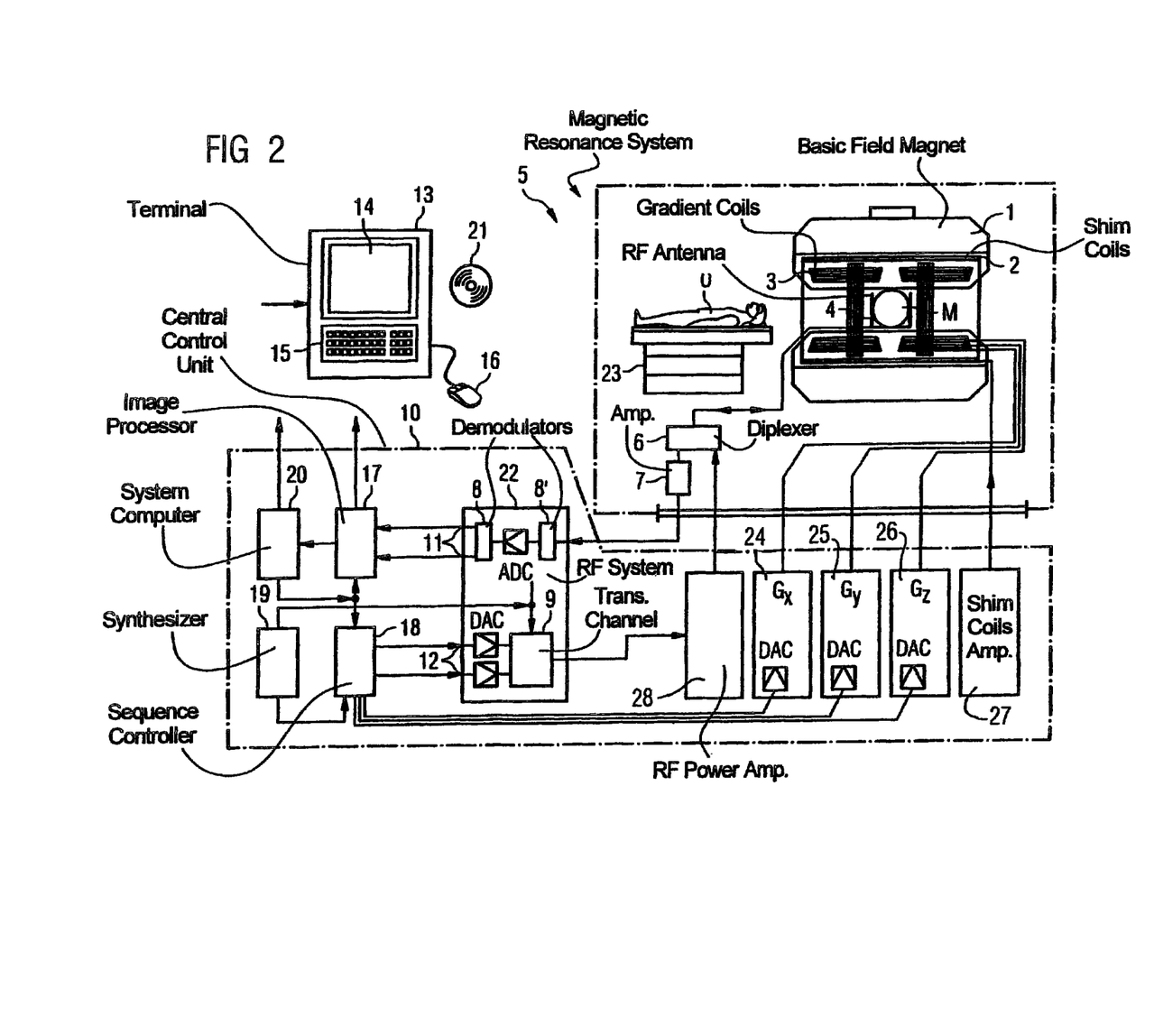
FIG. 2 schematically illustrates a magnetic resonance system according to the invention.

FIG. 2 shows a schematic representation of a magnetic resonance system 5 (a magnetic resonance imaging or magnetic resonance tomography apparatus). A basic field magnet 1 generates a temporally constant, strong magnetic field for polarization or alignment of the nuclear spins in an examination region of an examination subject U, for example a part of a human body that is to be examined that lies on a table 23 and is moved into the magnetic resonance system 5. The high homogeneity of the basic magnetic field that is required for the nuclear magnetic resonance measurement is defined in a typically spherical measurement volume M into which the parts of the human body that are to be examined are introduced. To support the homogeneity requirements, and in particular to eliminate temporally variable influences, shim plates made of ferromagnetic material are mounted at a suitable point. Temporally variable influences are eliminated via shim coils 2 and a suitable controller 27 for the shim coils 2.

A cylindrical gradient coil system 3 that has three sub-windings is used in the basic magnetic field 1. Each sub-winding is supplied by a corresponding amplifier 24-26 with current to generate a linear gradient field in the respective direction of a Cartesian coordinate system. The first sub-winding of the gradient field system 3 thereby generates a gradient $G_x$ in the x-direction; the second sub-winding generates a gradient $G_y$ in the y-direction; and the third sub-winding generates a gradient $G_z$ in the z-direction. The amplifiers 24-26 each include a digital/analog converter (DAC) which is controlled by a sequence controller 18 for time-accurate generation of gradient pulses.

Located within the gradient field system 3 is a radio-frequency antenna 4 which converts the radio-frequency pulses emitted by a radio-frequency power amplifier into an alternating magnetic field to excite the nuclei and align the nuclear spins of the subject to be examined or, respectively, of the region of the subject that is to be examined. The radio-frequency antenna 4 comprises one or more RF transmission coils and one or more RF reception coils in the form of an arrangement (annular, linear or matrix-like, for example) of coils. The alternating field emanating from the processing nuclear spins—i.e. normally the nuclear spin echo signals caused by a pulse sequence made up of one or more radio-frequency pulses and one or more gradient pulses—is also transduced by the RF reception coils of the radio-frequency antenna 4 into a voltage (measurement signal) which is supplied via an amplifier 7 to a radio-frequency reception channel 8, 8' of a radio-frequency system 22. The radio-frequency system 22 furthermore has a transmission channel 9 in which the radio-frequency pulses are generated for the excitation of the nuclear magnetic resonance. The respective radio-frequency pulses are represented digitally in the sequence controller 18 as a series of complex numbers based on a pulse sequence predetermined by the system computer 20. This number series is supplied as real part and imaginary part via respective inputs 12 to a digital/analog converter (DAC) in the radio-frequency system 22, and from this to the transmission channel 9. In the transmission channel 9 the pulse sequences are modulated on a radio-frequency carrier signal whose base frequency corresponds to the resonance frequency of the nuclear spins in the measurement volume. The modulated pulse sequences are supplied to the RF transmission coil of the radio-frequency antenna 4 via an amplifier 28.

The switch-over from transmission operation to reception operation takes place via a transmission/reception diplexer 6. The RF transmission coil of the radio-frequency antenna 4 radiates the radio-frequency pulses into the measurement volume M to excite the nuclear spins and samples resulting echo signals via the RF reception coils. The correspondingly acquired magnetic resonance signals (also called echo signals) are phase-sensitively demodulated at an intermediate frequency in a first demodulator 8' of the reception channel of the radio-frequency system 22 and are digitized in the analog/digital converter (ADC). This signal is further demodulated to a frequency of zero. The demodulation to a frequency of zero and the separation into real part and imaginary part occur after the digitization in the digital domain in a second demodulator 8 which outputs the demodulated data via outputs 11 to an image computer 17. An MR image is reconstructed by the image computer 17 from the measurement data acquired in such a manner. The administration of the measurement data, the image data and the control programs takes place via the system computer 20. Based on a specification with control programs, the sequence controller 18 controls the generation of the respective desired pulse sequences and the corresponding scanning of k-space. In particular, the sequence controller 18 controls the accurately-timed switching of the gradients, the emission of the radio-frequency pulses (such as RF excitation pulses and preparation pulses) with defined phase amplitude and the reception of the echo signals. The time base for the radio-frequency system 22 and the sequence controller 18 is provided by a synthesizer 19. The selection of corresponding control programs to generate an MR image (which is stored on a DVD 21, for example) as well as other inputs on the part of the user and the presentation of the generated MR image take place via a terminal 13 which comprises input means (for example a keyboard 15 and/or a mouse 16) to enable an input and display means (a monitor 14, for example) to enable a display. For example, via the input means a user can also select an examination region to be examined and a first region according to the invention (and therefore also the second region that covers k-space corresponding to the examination region that is not covered by the first region), as well as the type and frequency of preparation pulses to be applied in the regions.

Figure 3:
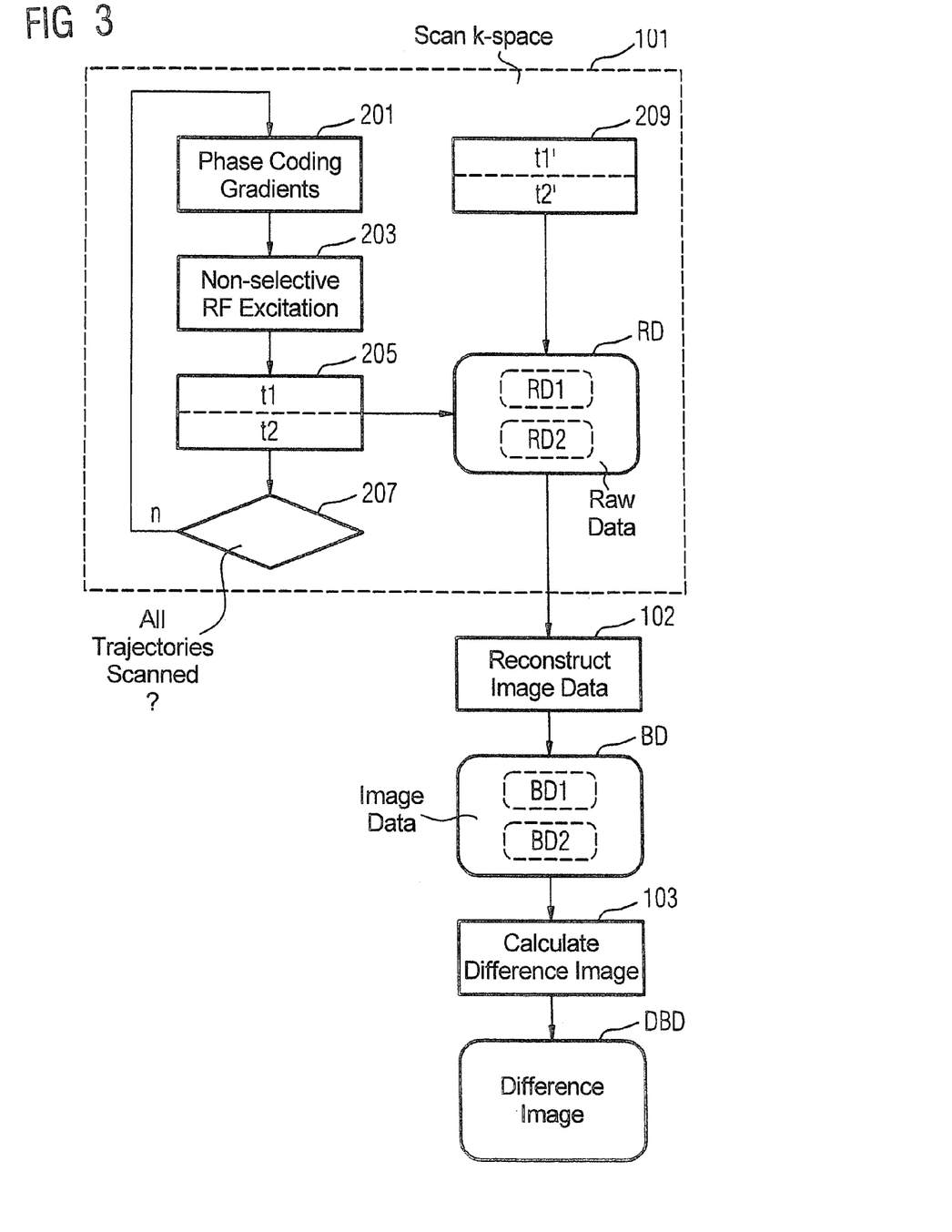
FIG. 3 is a flow chart of an embodiment of a method to create image data sets which can be used in connection, according to the invention.

A flowchart of an embodiment of a method to create an image data set that can be used in connection with the invention is schematically depicted in FIG. 3.

K-space corresponding to the examination region to be imaged is read out (i.e., data entries are made therein) in a first step 101 to create an image data set.

For this purpose, at least two phase coding gradients ($G_x$, $G_y$, $G_z$) are switched in a respective spatial direction by means of a gradient system of the magnetic resonance system (Block 201), and a non-slice-selective RF excitation pulse is radiated by means of a radio-frequency antenna of the magnetic resonance system (Block 202). If three phase coding gradients are switched, a three-dimensional image data set can be reconstructed in a conventional manner from the acquired raw data. If only two phase coding gradients are switched, a projection data set can be reconstructed.

After a time t1 after the last radiated excitation pulse, in which the phase coding gradients switched in Block 201 have already reached their full strength, echo signals are acquired by means of the radio-frequency antenna and—in an evaluation unit of the magnetic resonance system, for example a system computer of the magnetic resonance system—are stored as raw data points RD along the radial k-space trajectory predetermined by the strength of the phase coding gradients.

In one embodiment of this method, only echo signals after the time t1 are acquired and stored as raw data in the raw data set RD. In a further embodiment, after the time t1 after each RF excitation pulse first echo signals are acquired and stored as raw data in a first raw data set RD1, and furthermore after a time t2 after the same RF excitation pulse at least one second echo signal is acquired and stored as an additional raw data point in a second raw data set RD2, wherein t2>t1. The second echo signal is hereby generated in a known manner, for example by reversing the polarity of the gradients.

After all desired echo signals are acquired after an RF excitation pulse, and therefore after the corresponding k-space trajectory(y/ies) have been read out, in Step 207 a check is made as to whether k-space corresponding to the imaging area has thus already been read out or not along radial k-space trajectories in a first region (depending on the time t1). If not ("n"), Block 201 is begun again, wherein phase coding gradients differing from the previously used phase coding gradients are switched.

K-space corresponding to the imaging area and that is not covered by the first region of k-space—which first region is scanned by Blocks 201 through 205—is read out at an arbitrary point in time, or also at various points in time before, between or after the readout of the radial k-space trajectories, for example point by point by means of a single point imaging method (RASP, for example) or in another known manner (Block 209), and is likewise stored in the raw data set RD. If the raw data points which include the k-space center are hereby registered in a Cartesian manner, what is known as a regridding before the reconstruction of image data is superfluous.

Given the readout of k-space corresponding to the imaging area, the phase coding gradients can be varied continuously between the radiation of a first RF excitation pulse to acquire raw data points raw data points of k-space corresponding to the examination region and a second RF excitation pulse to acquire additional raw data points of k-space corresponding to the imaging area. This means that the phase coding gradients are not ramped down after every acquisition of a radial k-space trajectory and ramped up again for the acquisition of the next k-space trajectory; rather, the phase coding gradients are only ramped up or, respectively, down further from the already assumed strength, until the strength required for the next acquisition is achieved. The eddy currents induced by the current flow of the gradient system that is required to generate the phase coding gradients can thus be reduced, which reduces the formation of noise which is caused by the forces that the eddy currents impinge upon the gradient system.

It is advantageous to arrange the k-space trajectories to be read out such that the strength of the phase coding gradients must respectively only be varied as little as possible, whereby the noises caused by the change of the phase coding gradients can be further reduced in the measurement volume M of the magnetic resonance system.

Analogous to the exemplary embodiments already stated above, given the raw data points that are not read out in a different manner (for example by means of single point imaging methods) and which comprise the k-space center, after each RF excitation pulse a raw data point can be read out either only after a first echo time t1' and be stored in the first raw data set RD1; or after a first echo time t1' a first raw data point can be read out and stored in the first raw data set RD1 and after a second echo time t2'—with t1'<t2'—a second raw data point is read out and stored in the second raw data set RD2. The generation of the second echo thereby takes place again in the known manner.

In a further Step 102, an image data set BD is reconstructed from the acquired raw data points which are stored in the raw data set RD, for example by the evaluation device of the magnetic resonance system using a Fourier transformation.

If a first and second raw data sets RD1 and RD2 have been acquired and stored, analogously a first image data set BD1 can be reconstructed from the first raw data set RD1 and an additional, second image data set BD2 can be reconstructed from the second raw data set RD2.

In a further exemplary embodiment, in the case in which a first and second raw data sets RD1 and RD2 have been acquired and a first and additional, second image data set BD1 and BD2 have been reconstructed from these, a difference image DBD can be calculated from this first and second image data set BD1 and BD2 (Step 103). From the different echo times t1 and t2 with which the first and second raw data set RD1 and RD2 have been acquired, from the first and second image data sets BD1 and BD2 it is possible to generate a difference image in which tissue with a predetermined T2 are depicted exclusively.

For example, such a difference image DBD can occur via per-pixel subtraction of the second image data set BD2 from the first image data set BD1 (or vice versa), possibly with a suitable weighting of at least one of the two image data sets BD1 and BD2, for example: DBD=a*BD1−b*BD2, with a and b weighting factors.

The weighting factors a and b are advantageously dependent on a time constant prevailing in the imaging area imaged with the image data sets BD1 and BD2, in particular depending on the T2 value prevailing in the imaging area. The difference image DBD can therefore be created such that optimally exclusively tissue with a defined (short) T2 are displayed.

Figure 4:
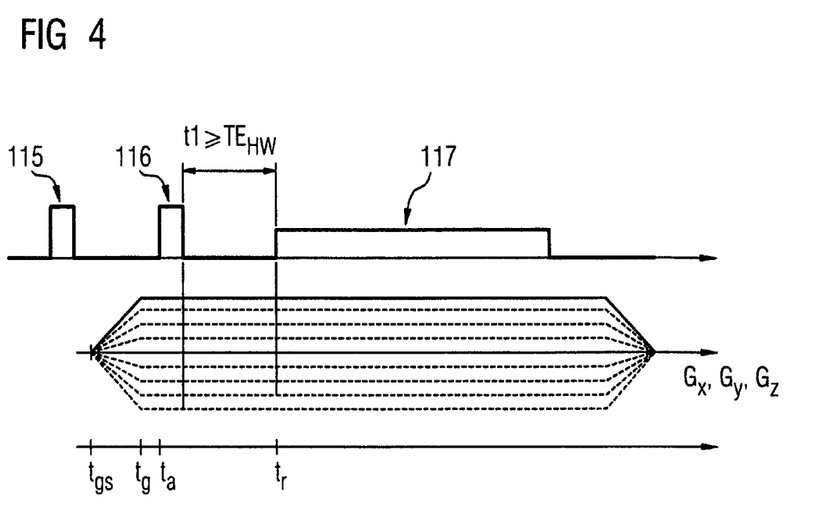
FIG. 4 schematically illustrates a portion of a sequence to acquire multiple raw data points on a radial k-space trajectory as it can be used in connection with the method according to the invention.

The part of a sequence according to the invention that serves to acquire multiple raw data points on a radial k-space trajectory is schematically presented in FIG. 4 (see FIG. 3, Blocks 201-205). At a point in time $t_{gs}$, at least two phase coding gradients $G_x$, $G_y$, $G_z$ are ramped up and reach their full strength at a point in time $t_g$. At a later point in time $t_a > t_g$, an RF excitation pulse 116 is radiated. After an echo time t1 after the RF excitation pulse 116 (that advantageously corresponds to the hardware-dependent minimum switching time between a transmission mode and a reception mode of a radio-frequency antenna $TE_{HW}$ that is used), the readout time period 117 to read out the echo signals is begun at the point in time $t_r$. Preparation pulses 115 can be switched before or in combination with every RF excitation pulse 116 (thus at every repetition of the sequence with other phase coding gradients), or only every n RF excitation pulses 116, wherein n is a number provided by a user of the magnetic resonance system.

In the exemplary embodiment shown in FIG. 4, the phase coding gradients are switched before the RF excitation pulse is radiated.

Figure 5:
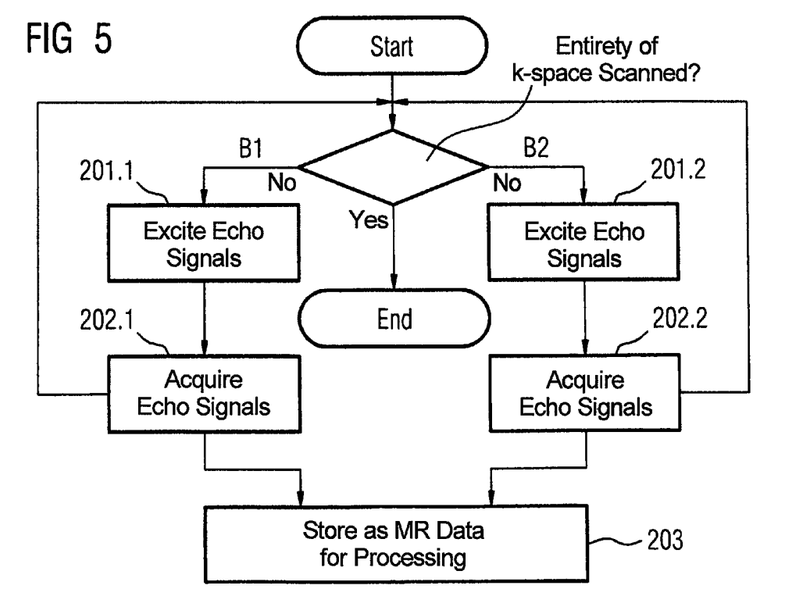
FIG. 5 is a flowchart of a scanning according to the invention of k-space corresponding to an examination region, and creation of magnetic resonance measurement data.

FIG. 5 schematically shows a flowchart plan of a scanning according to the invention of k-space corresponding to an examination region and generation of magnetic resonance measurement data.

The measurement starts ("start") after the examination region to be examined and the type of sequence with which k-space corresponding to the examination region should be scanned, as well as a first region B1 according to the invention and a second region B2 according to the invention, and a desired type of preparation pulses, have been established by a user.

K-space corresponding to the examination region is successively scanned by means of multiple repetitions of the sequence with switching of various gradients for spatial coding. Given those repetitions which scan k-space in the first region B1, successive echo signals are hereby excited in Step 201.1 in that an RF excitation pulse is radiated per repetition by a radio-frequency antenna of the magnetic resonance system. For example, a preparation pulse is hereby additionally radiated every N repetitions, which is why the ratio of preparation pulses radiated by the radio-frequency antenna of the magnetic resonance system to RF excitation pulses radiated by the radio-frequency antenna of the magnetic resonance system is equal to 1/N. In Step 202.1, the generated echo signals are acquired by means of the radio-frequency antenna after every radiated RF excitation pulse and are stored in Step 203 as magnetic resonance measurement data for additional processing.

In those repetitions which scan k-space in the second region B2, in Step 201.2 successive echo signals are likewise excited in that an RF excitation pulse is radiated per repetition by a radio-frequency antenna of the magnetic resonance system. In Step 201.2, however, fewer preparation pulses are radiated in the scanning of the second region B2 than in the first region B1 (Step 201.1), such that the ratio of preparation pulses radiated by the radio-frequency antenna of the magnetic resonance system to RF excitation pulses radiated by the radio-frequency antenna of the magnetic resonance system is smaller in Step 201.2 than in Step 201.1. For example, a preparation pulse can additionally be radiated every n repetitions (with n greater than N), which is why the ratio of preparation pulses radiated by the radio-frequency antenna of the magnetic resonance system to RF excitation pulses radiated by the radio-frequency antenna of the magnetic resonance system in the second region B2 is equal to 1/n (with 1/n>1/N). In Step 201.1, no preparation pulses at all can be radiated into the second region B2, which is why the ratio of preparation pulses radiated by the radio-frequency antenna of the magnetic resonance system to RF excitation pulses radiated by the radio-frequency antenna of the magnetic resonance system in the second region B2 would be equal to zero. After each radiated RF excitation pulse, the echo signals excited in Step 201.2 are acquired by means of the radio-frequency antenna (Step 202.2) and are stored as magnetic resonance measurement data for further processing in Step 203.

If the entirety of k-space corresponding to the examination region has been scanned in this manner, the method ends ("end").

Figure 6:
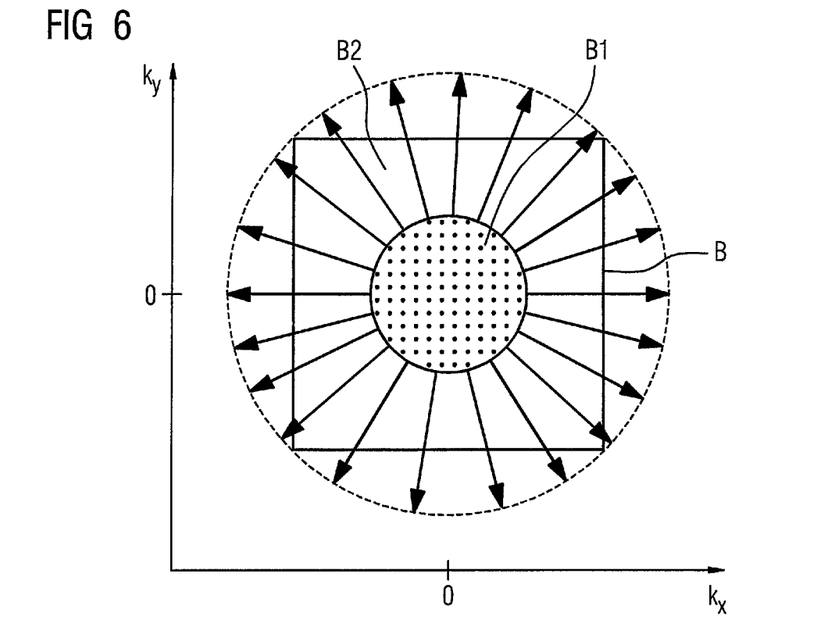
FIG. 6 schematically illustrates a division into a first region and second region for a possible embodiment of the invention.

A separation of k-space into a first region B1 and a second region B2 of k-space B corresponding to the examination region is schematically illustrated in FIG. 6 for a possible embodiment of the invention in connection with a method described using FIG. 3.

In the first region B1 comprising the k-space center, in the shown example k-space is read out in a Cartesian manner by means of single point measurements (for example with RASP). In contrast to this, the second region B2 is read out by means of a radial scan. Here the first region B1 is an approximately circular region B1 around the k-space center whose radius is dependent on the time t1 (described above) which extends after a radiated RF excitation pulse until the acquisition of the following echo signals. The second region B2 covers the portion of k-space B (corresponding to the examination region) that is not covered by the first region B1.

In this exemplary embodiment, the second region B2 corresponds to approximately 80% of the repetitions (excitations and acquisitions) required to cover the entirety of k-space corresponding to the examination region. By reducing the number of preparation pulses in relation to the RF excitation pulses in the second region in comparison to the first region, a large time savings is thus enabled and the entire measurement time can be significantly reduced.

For example, if a water or fat saturation is desired and corresponding preparation pulses are used to suppress the unwanted signals, in the prior art these are radiated approximately every five to 20 excitations. Given other sequences with longer echo times than the sequence described here using FIG. 3, one preparation pulse is normally radiated at every excitation. For example, given the sequence described using FIG. 3, in most cases the gradients must be ramped down before each preparation pulse, whereby approximately 30 additional milliseconds per preparation pulse are required for the measurement. Given T1 or T2 preparation pulses, the additional required time per preparation pulse is even longer since this must respectively wait for the relaxation time of the nuclear spins. It can therefore occur that—for example given a duration for a preparation pulse of 800 milliseconds per measurement effectively lasting 200 milliseconds—the total measurement time is multiplied fivefold.

In the example of FIG. 6 that is shown above, the extension of the measurement time can be reduced to only approximately 1.5 times or, respectively, 2.5 times (in comparison to the fivefold multiplication in the prior art that is just cited) in that, as in the prior art, preparation pulses are furthermore additionally radiated approximately every 200 milliseconds in the first region, but are radiated only every 1000 milliseconds or are no longer radiated at all in the second region (80% of the repetitions). The transmission power that is also required and radiated at the examination subject—and the SAR that is therefore applied—is thereby also drastically reduced.

Figure 7:
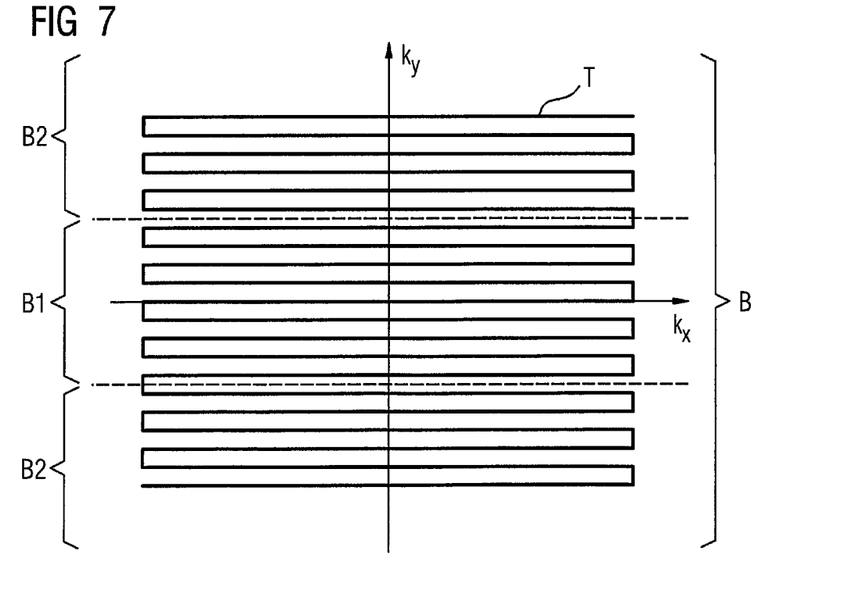
FIG. 7 schematically illustrates an additional division into a first region and second region for another possible embodiment of the invention.

FIG. 7 shows a schematic illustration of a further separation into a first and second region for another possible embodiment of the invention in which k-space is scanned along k-space lines, for example as is the case in typical gradient echo sequences (GRE) or also (turbo) spin echo sequences ((T)SE). K-space B corresponding to the examination region is hereby read out along the k-space lines illustrated by the trajectory T. The first region B1 hereby comprises those k-space lines with a predetermined maximum distance from the k-space center (intersection point of the shown k-space directions $k_x$ and $k_y$), while the second region B2 comprises the outer k-space lines.

In all exemplary embodiments, according to the invention more preparation pulses are radiated in every first region which comprises the k-space center than in the associated second region. In particular, no preparation pulses at all can also be radiated in the second region. However, the ratio of radiated preparation pulses to radiated RF excitation pulses can also be selected to be twice or three times as large in the first region than in the second region.

In an exemplary embodiment, the preparation pulses can hereby be respectively radiated with uniform distribution in the first region and in the second region. For example, in the first region N excitations and in the second region every n excitations can be implemented with radiation of a preparation pulse, wherein N is smaller than n and N and n are each a natural number, for example. For example, n can be selected equal to a multiple of N.

The optimal ratios of radiated preparation pulses to radiated RF excitation pulses in the first region and in the second region can be selected depending on the requirement for the quality of the measurement data, and therefore the achievable image quality of the MR images that are reconstructed from the measurement data and/or the quality of the respective function of the preparation pulses (for example suppression of unwanted signals such as signals of fat and/or water).

For example, given use of preparation pulses to suppress fat signals in connection with an acquisition of the measurement data described using FIGS. 3 and 6, with a radiation of preparation pulses every 50 milliseconds in the first region and every 50 milliseconds in the second region (i) or every 100 milliseconds in the second region (ii) or every 150 milliseconds in the second region (iii), first attempts have yielded that the total measurement time could be shortened from 4.5 minutes (i) to 3.5 minutes (ii) or to 3 minutes (iii), wherein no difference in the achieved fat saturation or image quality was detectable between the MR images reconstructed from (i) and (ii). The MR image reconstructed from (iii) had a similarly comparable image quality but a somewhat more weakly pronounced fat saturation.

Analogous attempts with T2 preparation pulses show similar results. For example, again in connection with a sequence according to FIGS. 3 and 6, measurement data are acquired with preparation pulses radiated every 200 milliseconds in the first region and every 200 milliseconds (I), every 400 milliseconds (II) or every 600 milliseconds (III) in the second region. The measurement time could be reduced from 18 minutes (I) to 11 minutes (II) or to 8 minutes (III). The desired T2 contrast was easy to recognize in the MR images reconstructed from (I) and (II), albeit somewhat more strongly pronounced in (I). Only a slight effect of the T2 preparation pulses was apparent in the MR image reconstructed from (III).

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to generate magnetic resonance (MR) data of an examination region of an examination subject, comprising:

operating an MR data acquisition unit having a measurement volume in which the examination region of the examination subject is located, to generate echo signals originating from said examination region by radiating a plurality of radio-frequency (RF) excitation pulses successively with an RF antenna of said MR data acquisition unit, and generating respectively different magnetic field gradients with a gradient coil system of said MR data acquisition unit to spatially encode said echo signals until data entries corresponding to said examination region have been entered into k-space in a memory, and radiating preparation pulses into the examination region of the examination subject with said RF antenna with a ratio of said preparation pulses to said RF excitation pulses being larger in a first region of k-space corresponding to said examination region and that comprises at least a center of k-space, than a second region of k-space corresponding to said examination region, said second region not being covered by said first region and wherein said first region is a region surrounding said k-space center with a radius depending on a time t1 that follows after a radiated RF excitation pulse up to acquisition of a following echo signal;

acquiring said echo signals with an RF reception antenna after each radiated RF excitation pulse; and making said entries in k-space available from said memory as a measurement data file.

2. The method as claimed in claim 1 comprising selecting pulses for radiation as said preparation pulses from the group consisting of T1 preparation pulses, T2 preparation pulses, and preparation pulses configured to suppress unwanted signals.

3. The method as claimed in claim 1 comprising radiating no preparation pulses in said second region.

4. The method as claimed in claim 1 comprising selecting said ratio to be at least twice as large in said first region as in said second region.

5. The method as claimed in claim 1 comprising radiating said preparation pulses with a uniform distribution in said first region and in said second region.

6. The method as claimed in claim 1 wherein said first region comprises lines of k-space with a predetermined maximum distance from said center of k-space.

7. A magnetic resonance (MR) apparatus to generate MR data of an examination region of an examination subject, comprising:

an MR data acquisition unit having a measurement volume in which the examination region of the examination subject is located;

a control unit configured to operate said MR data acquisition unit to generate echo signals originating from said examination region by radiating a plurality of radio-frequency (RF) excitation pulses successively with an RF antenna of said MR data acquisition unit, and generating respectively different magnetic field gradients with a gradient coil system of said MR data acquisition unit to spatially encode said echo signals until data entries corresponding to said examination region have been entered into k-space in a memory, and radiating preparation pulses into the examination region of the examination subject with said RF antenna with a ratio of said preparation pulses to said RF excitation pulses being larger in a first region of k-space corresponding to said examination region and that comprises at least a center of k-space, than a second region of k-space corresponding to said examination region, said second region not being covered by said first region and wherein said first region is a region surrounding said k-space center with a radius depending on a time t1 that follows after a radiated RF excitation pulse up to acquisition of a following echo signal;

acquire said echo signals with an RF reception antenna after each radiated RF excitation pulse; and said control unit being configured to operate said MR data acquisition unit to make said entries in k-space available from said memory as a measurement data file.

8. A non-transitory, computer-readable data storage medium encoded with programming instructions, said data storage medium being loaded into a computerized control and evaluation system of a magnetic resonance (MR) apparatus comprising an MR data acquisition unit, said programming instructions causing said computerized control and evaluation unit to operate said MR apparatus to:

operate the MR data acquisition unit, with an examination region of an examination subject is located in a measurement volume thereof, to generate echo signals originating from said examination region by radiating a plurality of radio-frequency (RF) excitation pulses successively with an RF antenna of said MR data acquisition unit, and generating respectively different magnetic field gradients with a gradient coil system of said MR data acquisition unit to spatially encode said echo signals until data entries corresponding to said examination region have been entered into k-space in a memory, and radiating preparation pulses into the examination region of the examination subject with said RF antenna with a ratio of said preparation pulses to said RF excitation pulses being larger in a first region of k-space corresponding to said examination region and that comprises at least a center of k-space, than a second region of k-space corresponding to said examination region, said second region not being covered by said first region and wherein said first region is a region surrounding said k-space center with a radius depending on a time t1 that follows after a radiated RF excitation pulse up to acquisition of a following echo signal;

acquire said echo signals with an RF reception antenna after each radiated RF excitation pulse; and make said entries in k-space available from said memory as a measurement data file.

9. A method as claimed in claim 1 wherein said time t1 is at least as long as a hardware-dependent minimum switching time between a transmission mode and a reception mode of said RF antenna.

10. A method as claimed in claim 7 wherein said time t1 is at least as long as a hardware-dependent minimum switching time between a transmission mode and a reception mode of said RF antenna.

11. A method as claimed in claim 8 wherein said time t1 is at least as long as a hardware-dependent minimum switching time between a transmission mode and a reception mode of said RF antenna.

* * * * *